US010231637B2

(12) United States Patent
Voth et al.

(10) Patent No.: US 10,231,637 B2
(45) Date of Patent: Mar. 19, 2019

(54) NON-CONTACT MAPPING SYSTEM AND METHOD

(71) Applicant: St. Jude Medical, Atrial Fibrillation Division, Inc., St. Paul, MN (US)

(72) Inventors: Eric J. Voth, Maplewood, MN (US); Jiang Qian, Edina, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 333 days.

(21) Appl. No.: 14/766,930

(22) PCT Filed: Mar. 5, 2014

(86) PCT No.: PCT/US2014/020716
§ 371 (c)(1),
(2) Date: Aug. 10, 2015

(87) PCT Pub. No.: WO2014/164129
PCT Pub. Date: Oct. 9, 2014

(65) Prior Publication Data
US 2015/0366481 A1  Dec. 24, 2015

Related U.S. Application Data

(60) Provisional application No. 61/777,397, filed on Mar. 12, 2013.

(51) Int. Cl.
*A61B 5/04* (2006.01)
*A61B 5/042* (2006.01)
(Continued)

(52) U.S. Cl.
CPC .......... *A61B 5/04012* (2013.01); *A61B 5/044* (2013.01); *A61B 5/0422* (2013.01); *A61B 5/0432* (2013.01); *A61B 5/063* (2013.01)

(58) Field of Classification Search
None
See application file for complete search history.

(56) References Cited

U.S. PATENT DOCUMENTS 6,226,542 B1 * 5/2001 Reisfeld ............. A61B 5/04011
600/407
6,633,773 B1  10/2003 Reisfeld
(Continued)

FOREIGN PATENT DOCUMENTS

WO  2000/007501  2/2000

*Primary Examiner* — Katherine Fernandez
*Assistant Examiner* — Yi-Shan Yang
(74) *Attorney, Agent, or Firm* — Armstrong Teasdale LLP

(57) ABSTRACT

In a system and method for non-contact mapping of an anatomic structure, the spatial position of an electrode is determined independent of a previously generated three-dimensional model of the anatomic structure. A position of the electrode relative to a boundary surface of the model is determined, along with a corresponding point on the boundary surface of the three-dimensional model that is closest to the relative electrode position. A signed distance (d) of the relative electrode position from the corresponding closest point on the boundary surface is determined, wherein a positive signed distance indicates the relative electrode position is exterior to the model. In such an instance, the boundary surface is perturbed (e.g., expanded outward) at least in part as a function of the signed distance (d) until the relative electrode position lies interior to the model.

10 Claims, 8 Drawing Sheets

(51) Int. Cl.
   *A61B 5/0432* (2006.01)
   *A61B 5/044* (2006.01)
   *A61B 5/06* (2006.01)

(56) References Cited

U.S. PATENT DOCUMENTS

| | | | |
|---|---|---|---|
| 6,674,904 B1 * | 1/2004 | McQueen | G06K 9/4619 |
| | | | 382/173 |
| 7,263,397 B2 | 8/2007 | Hauck et al. | |
| 7,920,140 B2 * | 4/2011 | Liepa | G06T 17/20 |
| | | | 345/419 |
| 2001/0009974 A1 * | 7/2001 | Reisfeld | A61B 5/04011 |
| | | | 600/407 |
| 2004/0254437 A1 * | 12/2004 | Hauck | A61B 5/0422 |
| | | | 600/374 |
| 2005/0203375 A1 * | 9/2005 | Willis | A61B 5/0422 |
| | | | 600/407 |
| 2010/0168550 A1 | 7/2010 | Byrd et al. | |
| 2010/0280399 A1 | 11/2010 | Francis et al. | |
| 2010/0286551 A1 | 11/2010 | Harlev et al. | |
| 2013/0135305 A1 * | 5/2013 | Bystrov | G06T 19/20 |
| | | | 345/420 |

* cited by examiner

NON-CONTACT MAPPING SYSTEM AND METHOD

BACKGROUND OF THE DISCLOSURE

A. Field of the Disclosure

The present disclosure relates generally to mapping systems and methods for mapping anatomic structures, and more particularly to such mapping systems and methods which use a non-contact catheter.

B. Background Art

Cardiac tachyarrhythmia is often caused by conduction defects which interfere with the normal propagation of electrical signals in a patient's heart. These arrhythmias may be treated electrically, pharmacologically or surgically. The optimal therapeutic approach to treat a particular tachyarrhythmia depends upon the nature and location of the underlying conduction defect. For this reason electrophysiologic (EP) mapping is commonly used to explore the electrical activity of the heart during a tachyarrhythmic episode. The typical electrophysiologic mapping procedure involves positioning an electrode system within the heart. Electrical measurements are made which reveal the electrical propagation of activity in the heart. If ablation is the indicated therapy, then a therapy catheter is positioned at the desired location within the heart and energy is delivered to the therapy catheter to ablate the tissue.

Three-dimensional mapping techniques typically include either contact mapping or non-contact mapping. In contact mapping, one or more catheters including one or more electrodes are advanced into the heart. Electrophysiological signals resulting from the electrical activity of the heart are obtained by the one or more electrodes with at least the catheter and in some methods the electrodes in contact with the endocardial surface of the heart—e.g., a particular heart chamber. Multiple data points are obtained on the internal surface of the heart and are used to construct a three-dimensional depiction of the heart.

For non-contact mapping, one or more catheters carrying one or more electrodes are located within the heart in spaced proximity to the endocardial surface of the heart. Signals are detected by the electrodes and used to correlate the spatial positions of the electrodes relative to a previously determined three-dimensional model of the heart (or portion of the heart being mapped). Conventional modeling systems exist for generating such a three-dimensional model of the heart utilizing technology such as CT scan, MRI, radar imaging, x-ray imaging, and fluoroscopic imaging. Such data is often processed using a three-dimensional modeling technique—commonly some form of a Boundary Element Method (BEM) such as a spline BEM or linear BEM. The imaging process is performed hours and in some cases days in advance of the treatment and/or surgery.

The system must determine, using the signals detected by the electrodes, the relative position of each of the electrodes and then correlate such data with the previously generated three-dimensional model. Due to any number of factors associated with such a mapping technique, such as the actual distance of the electrodes away from the endocardial surface, the movement of the endocardial surface as signals are being detected by the electrodes, etc., the determined relative electrode positions may be exterior to the boundary surface of the three-dimensional model. Prior non-contact mapping systems, and in particular the inverse problem of electrocardiography and the underlying equations of the BEM in such systems, make the assumption that the electrodes are contained with the boundary surface of the three-dimensional model. It has occurred, though, that erroneous and perplexing reconstructions of the heart electrophysiology can result from such assumptions when the relative positions of the electrodes indeed lie exterior to the boundary surface of the three-dimensional model.

It is thus desirable for a mapping system (and more particularly a non-contact mapping system) and method that is used for mapping an anatomic structure to not assume all relative positions of the measurement electrodes lie within the boundary surface of a three-dimensional model of the anatomic structure. It is further desirable that such a mapping system and method can make adjustments to account for situations in which the relative positions of one or more measurement electrodes lie exterior to the boundary surface of the three-dimensional model of the anatomic structure.

BRIEF SUMMARY OF THE DISCLOSURE

In one embodiment, a computer implemented method for modeling the spatial position of an electrode relative to a three-dimensional model of an anatomic structure is described. The three-dimensional model has a boundary surface. The method includes: locating the electrode at a position that is at least one of abutting and in spaced proximity to the anatomic structure; determining a three-dimensional spatial position of the electrode independent of the three-dimensional model of the anatomic structure; determining, based at least in part on the determined three-dimensional spatial location of the electrode, a position of the electrode relative to the boundary surface of the three-dimensional model; comparing the determined relative electrode position to a tolerance criterion for the determined relative electrode position; and based at least in part on this comparison not meeting the tolerance criterion, at least one of altering the determined relative electrode position and altering the boundary surface of the three-dimensional model relative to the determined relative electrode position. In such an embodiment, the boundary surface defines an interior of the three-dimensional model and an exterior of the three-dimensional model. The tolerance criterion corresponds to the relative position of the electrode being one of on the boundary surface of the three-dimensional model and on the interior of the three-dimensional model. The altering step comprises, in response to the relative position of the electrode being exterior to the boundary surface, at least one of altering the relative electrode position and altering the boundary surface of the three-dimensional model relative to the relative electrode position such that subsequent to the altering step the relative electrode position is one of on the boundary surface of the three-dimensional model and on the interior of the three-dimensional model.

In such an embodiment, the altering step comprises translating at least a portion of the boundary surface of the three-dimensional model toward the determined relative electrode position until the tolerance criterion is satisfied.

In such an embodiment, the step of translating at least a portion of the boundary surface of the three-dimensional model toward the determined relative electrode position comprises translating at least a portion of the boundary surface of the three-dimensional model toward the determined relative electrode position an amount greater than or equal to a distance between the determined relative electrode position and the boundary surface of the three-dimensional model.

In such an embodiment, the method further comprises determining a point on the boundary surface of the three-dimensional model closest to the determined relative electrode position. A distance is determined between the point on the boundary surface and the determined relative electrode position. Satisfaction of the tolerance criterion is at least in part a function of the distance between the point on the boundary surface and the determined relative electrode position.

In such an embodiment, the three-dimensional model comprises a spline model including a plurality of grid cells with each grid cell including a plurality of vertices. The step of translating at least a portion of the surface of the three-dimensional model toward the determined relative electrode position comprises translating, in a direction parallel to a vector from the determined point on the boundary surface to the determined relative electrode position, the plurality of vertices of a grid cell within which the determined point lies by an amount greater than or equal to the determined distance between the point and the determined relative electrode position.

In such an embodiment, the step of translating the plurality of vertices of a grid cell within which the determined point lies comprises translating the plurality of vertices of the grid cell by an amount equal to the sum of a threshold value and the determined distance between the determined relative electrode position and the determined point on the surface such that subsequent to the translating step the relative electrode position is interior of the three-dimensional model and spaced from the boundary surface a distance equal to or greater than the threshold value.

In such an embodiment, the locating step comprises locating a plurality of electrodes at respective positions that are at least one of abutting and in spaced proximity to the anatomic structure. The determining and comparing steps are conducted for each of the electrodes, wherein in the event that more than one of the determined points lie within one of the grid cells, the translating step is conducted one of a) a single instance by determining which of the relative electrode positions of the electrodes is furthest away from its respective determined point and translating the plurality of vertices of the grid cell by an amount greater than or equal to the determined distance between the determined point and the determined relative position of the further away electrode and b) for each relative electrode position until the relative positions of all electrodes having a respective determined point within the grid cell are subjected to the translating step.

In another such embodiment, the three-dimensional model comprises a polygon mesh including a plurality of cells each having a plurality of vertices. The step of translating at least a portion of the boundary surface of the three-dimensional model toward the determined relative electrode position comprises translating each vertex that is less than a determined distance b along the boundary surface away from the determined point outward by a determined amount. The determined amount of translation is a function of at least one of a) a distance r of each respective vertex along the boundary surface to the point on the boundary surface and b) the determined distance of the relative electrode position from the point on the boundary.

In such an embodiment, the determined amount of outward translation of each vertex to be translated is a function of both a) the distance r of each respective vertex along the boundary surface to the determined point on the boundary surface and b) the determined distance of the relative electrode position from the determined point on the boundary.

In such an embodiment, the three-dimensional model comprises a polygon mesh including a plurality of cells each having a plurality of vertices. The step of translating at least a portion of the boundary surface of the three-dimensional model toward the determined relative electrode position comprises: determining the vertex from among the plurality of vertices that is nearest to the determined point on the boundary surface; overlaying the boundary surface of the three-dimensional model with a control mesh having cells that are substantially larger than the cells of the three-dimensional model, each cell of the control mesh having a plurality of nodes, the control mesh including a main node in common with said determined vertex; and translating the control mesh at the main node thereof.

In such an embodiment, the method is for non-contact mapping of an anatomic structure and further comprises generating a three-dimensional model of the anatomic structure and locating the electrode at a position within the anatomic structure in spaced proximity to an inner surface of the anatomic structure. The previously described determining steps, comparing step and altering step are all performed using the generated three-dimensional model of the anatomic structure.

In such an embodiment, the locating step comprises inserting a multi-electrode catheter into the anatomic structure, with each of the electrodes in spaced proximity to the inner surface of the anatomic structure, and performing each of the previously described determining steps, comparing step and altering step for each of the electrodes.

In another embodiment, a non-contact system for mapping electrode data to a three-dimensional model of an anatomic structure generally comprises at least one electrode positionable relative to the anatomic structure and a computing device configured to receive signals from the at least one electrode positioned relative to the anatomic structure. The computing device includes a processor and at least one memory device coupled to the processor. The memory device stores the three-dimensional model of the anatomic structure and computer-executable instructions that, when executed by the processor, cause the controller to: determine a position of the electrode relative to a boundary surface of the three-dimensional model; compare the determined relative electrode position to a tolerance criterion for said determined relative electrode position; and, based at least in part on this comparison not meeting the tolerance criterion, at least one of alter the determined relative electrode position and alter the boundary surface of the three-dimensional model relative to the determined relative electrode position. In such a system, the boundary surface defines a first side of the three-dimensional model and a second side of the three-dimensional model. The tolerance criterion corresponding to the relative position of the electrode is one of on the boundary surface of the three-dimensional model and on the first side of the three-dimensional model. The memory device stores computer-executable instructions that, when executed by the processor, cause the processor to at least one of alter the determined relative electrode position and alter the boundary surface of the three-dimensional model relative to the determined relative electrode position such that the relative electrode position is one of on the boundary surface of the three-dimensional model and on the first side of the three-dimensional model.

In such a system, the boundary surface defines an interior of the three-dimensional model and an exterior of the three-dimensional model. The tolerance criterion corresponding to the relative electrode position is one of on the boundary surface of the three-dimensional model and on the interior of the three-dimensional model. The memory device stores computer-executable instructions that, when executed by the processor, cause the processor to, in response to the relative electrode position being exterior to the boundary surface, at least one of alter the relative electrode position and alter the boundary surface of the three-dimensional model relative to the relative electrode position such that the relative electrode position is one of on the boundary surface of the three-dimensional model and on the interior of the three-dimensional model.

In such a system, the memory device stores computer-executable instructions that, when executed by the processor, cause the processor to alter the boundary surface of the three-dimensional model relative to the determined relative electrode position by translating at least a portion of the boundary surface of the three-dimensional model toward the determined relative electrode position until the tolerance criterion is satisfied.

In such a system, translating at least a portion of the boundary surface of the three-dimensional model toward the determined relative electrode position comprises translating at least a portion of the boundary surface of the three-dimensional model toward the determined relative electrode position an amount greater than or equal to a distance between the determined relative electrode position and the boundary surface of the three-dimensional model.

In such a system, the memory device further stores computer-executable instructions that, when executed by the processor, cause the computing device to: determine a point on the boundary surface of the three-dimensional model closest to the determined relative electrode position; and determine a distance between the point on the boundary surface and the determined relative electrode position, with satisfaction of the tolerance criterion being at least in part a function of the distance between the point on the boundary surface and the determined relative electrode position.

In such a system, the three-dimensional model comprises a spline model including a plurality of grid cells with each grid cell including a plurality of vertices. Translating at least a portion of the surface of the three-dimensional model toward the determined relative electrode position comprises translating, in a direction parallel to a vector from the point on the boundary surface to the determined relative electrode position, the plurality of vertices of a grid cell within which the determined point lies by an amount greater than or equal to the determined distance between the point and the determined relative electrode position.

In such a system, translating the plurality of vertices of a grid cell within which the determined point lies comprises translating the plurality of vertices of the grid cell by an amount equal to the sum of a threshold value and the determined distance between the determined relative electrode position and the determined point on the surface such that subsequent to the translating step the relative position of the electrode is interior of the three-dimensional model and spaced from the boundary surface a distance equal to or greater than the threshold value.

In such a system, the computing device is configured to receive signals from a plurality of electrodes located at respective positions that are at least one of abutting and in spaced proximity to the anatomic structure. The memory device stores computer-executable instructions that, when executed by the processor, cause the computing device to determine the relative electrode position, compare the determined relative electrode position, and determine a point on the boundary surface for each of the electrodes, wherein in the event that more than one of the determined points lie within one of the grid cells, the translating is conducted one of a) a single instance by determining which of the relative electrode positions is furthest away from its respective determined point and translating the plurality of vertices of the grid cell by an amount greater than or equal to the determined distance between the determined point and the determined relative electrode position of the further away electrode and b) for each relative electrode position until the relative electrode positions of all electrodes having a respective determined point within the grid cell are subjected to the translating step.

In another such system, the three-dimensional model comprises a polygon mesh including a plurality of cells each having a plurality of vertices. Translating at least a portion of the surface of the three-dimensional model toward the determined relative position of the electrode comprises translating each vertex that is less than a determined distance b along the boundary surface away from the determined point outward by a determined amount. The determined amount is a function of at least one of a) a distance r of each respective vertex along the boundary surface to the point on the boundary surface and b) the determined distance of the relative position of the electrode from the point on the boundary surface.

In such a system, the determined amount of outward translation of each vertex to be translated is a function of both a) the distance r of each respective vertex along the boundary surface to the point on the boundary surface and b) the determined distance of the relative position of the electrode from the point on the boundary surface.

In such a system, the three-dimensional model comprises a polygon mesh including a plurality of cells each having a plurality of vertices. Translating at least a portion of the surface of the three-dimensional model toward the determined relative position of the electrode comprises: determining the vertex from among the plurality of vertices that is nearest to the determined point on the boundary surface; overlaying the boundary surface of the three-dimensional model with a control mesh having cells that are substantially larger than the cells of the three-dimensional model, with each cell of the control mesh having a plurality of nodes and the control mesh including a main node in common with the determined vertex; and translating the control mesh at the main node thereof.

In yet another embodiment, a computer implemented method for non-contact mapping of anatomic structure generally comprises generating a three-dimensional computer model having a boundary surface separating a first side of the three-dimensional model from a second side of the three-dimensional model; positioning at least one electrode in proximity to the anatomic structure; determining, for each electrode, a spatial position of the electrode; determining, for each spatial electrode position, a position of the respective electrode relative to the boundary surface of the three-dimensional model; determining, for each relative electrode position, a corresponding point on the boundary surface of the three-dimensional model that is closest to the relative electrode position; determining, for each relative electrode position, a signed distance (d) from the corresponding closest point on the boundary surface to the relative electrode position, wherein a positive signed distance indicates the electrode position is on the second side of the three-dimensional model; and perturbing the boundary surface of the three-dimensional model at least in part as a function of the signed distance (d) of at least one of the relative electrode positions. In such a method, perturbing the boundary surface of the three-dimensional model comprises perturbing the boundary surface of the three-dimensional model such that the signed distance (d) corresponding to every relative electrode position is one of zero and less than zero following perturbing of the boundary surface.

In such a method, perturbing the boundary surface of the three-dimensional model comprises perturbing the boundary surface of the three-dimensional model such that following perturbing of the boundary surface the signed distance (d) corresponding to every relative electrode position is less than zero and an absolute value of the signed distance (d) corresponding to every relative electrode position is greater than a threshold value.

In such a method, the boundary surface of the three-dimensional model comprises a plurality of cells, each cell having a plurality of vertices. The step of perturbing the boundary surface comprises translating all vertices within a maximum distance (b) of each of the determined points corresponding to a relative electrode position having a signed distance (d) that is greater than zero.

In such a method, for each of the determined points corresponding to a relative electrode position having a signed distance (d) that is greater than zero, the maximum distance (b) is the lesser of a predetermined fixed maximum value and five times an absolute value of the signed distance (d) for the determined point.

In such a method, each translated vertex is translated a distance determined as a function of at least one of a) the signed distance d of the respective relative electrode position and b) a distance (r) of the vertex from the respective determined point.

In such a method, each translated vertex is translated a distance determined as a function of both a) the signed distance d of the respective relative electrode position and b) the distance (r) of the vertex from the respective determined point.

In such a method, each translated vertex is translated a distance determined using a cosine function.

In such a method, each translated vertex is translated a distance determined using the formula:

$d*(0.5+0.5 \cos(\pi r/b))$; where (d) is the signed distance of the respective relative electrode position from the corresponding determined point on the boundary surface, (r) is the distance of the vertex from the corresponding determined point on the boundary surface, and (b) is the maximum distance.

In such a method, the distance (r) is determined in Cartesian space.

In such a method, the distance (r) is determined along the boundary surface.

In such a method, the boundary surface is perturbed for each relative electrode position having a signed distance (d) greater than zero independent of the order in which each relative electrode position is determined.

In such a method, perturbing the boundary surface of the three-dimensional model comprises, for each cell in which a determined point corresponding to a relative electrode position having a signed distance of greater than zero lies, translating all vertices of the respective cell a distance at least equal to the signed distance (d) of the relative electrode position that is furthest from the boundary surface of the model.

The foregoing and other aspects, features, details, utilities and advantages of the present disclosure will be apparent from reading the following description and claims, and from reviewing the accompanying drawings.

BRIEF DESCRIPTION OF THE DRAWINGS

Corresponding reference characters indicate corresponding parts throughout the drawings.

DETAILED DESCRIPTION OF THE DISCLOSURE

The present disclosure relates generally to mapping systems and methods for mapping anatomic structures, such as the human heart or portions thereof, and more particularly to such mapping systems and methods which use a non-contact catheter having multiple electrodes. In particular embodiments, the systems and methods of the present disclosure improve correlation between one or more measurement electrodes located in proximity to the anatomic structure (e.g., inserted into a patient's heart) and a previously generated three-dimensional model of the anatomic structure. While the various embodiments herein are described in connection with mapping of a patient's heart, it is understood that the present disclosure is not limited to mapping of a heart, and that mapping of other anatomic structures is considered to be within the scope of the present disclosure.

Known systems and methods exist for generating a three-dimensional model of an anatomic structure such as the heart, including systems that utilize technology such as CT scanning, MRI, ultrasound imaging, radar imaging, x-ray imaging, and fluoroscopic imaging. The output of such data may be a plurality of x-y-z data coordinates, spherical coordinates and/or other formats to provide a three-dimensional image. Such imaging technology is often useful in diagnosis as well as preparing for a patient's treatment and/or surgery. The imaging process may be performed hours or days before treatment and/or surgery, or concomitantly with the treatment and/or surgery. Some three-dimensional models utilize a segmented approach, including for example a segmented CT or MRI scan image. A segmented model indicates that a subregion of a three-dimensional image has been digitally separated from a larger three-dimensional image, e.g., an image of the right atrium separated from the rest of the heart. Other methodologies and techniques for creating a three-dimensional model of a portion of the patient may also be utilized in accordance with the present disclosure.

Data acquired from the imaging process is typically used to partition the three-dimensional model into discrete surface elements to facilitate numerical computation during subsequent mapping and reconstruction. It is understood that various computational methods may be used to partition the three-dimensional model into discrete segments, such as finite differences, Finite Element Methods (FEM) and Boundary Element Methods (BEM) such as spline BEM or linear BEM. The three-dimensional model of the anatomic structure generally includes a boundary surface defined by the discrete segments, with the boundary surface thus defining an interior (broadly, a first side) of the three-dimensional model and an exterior (broadly, a second side) of the three-dimensional model of the anatomic structure.

Figure 1:
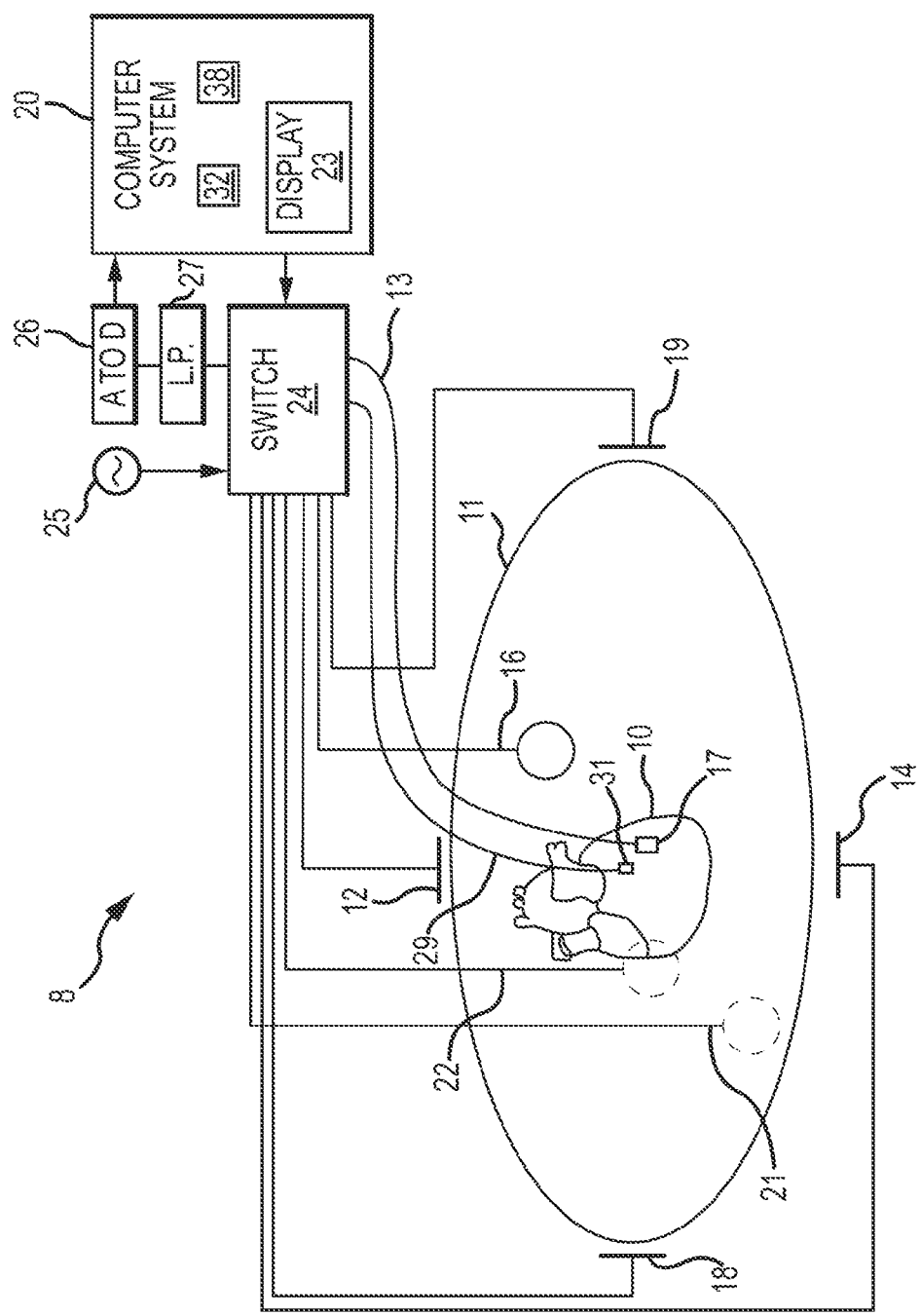
FIG. 1 is a schematic diagram of a system for performing a cardiac electrophysiology examination or ablation procedure wherein the location of one or more electrodes can be determined and recorded.
Figure 2:
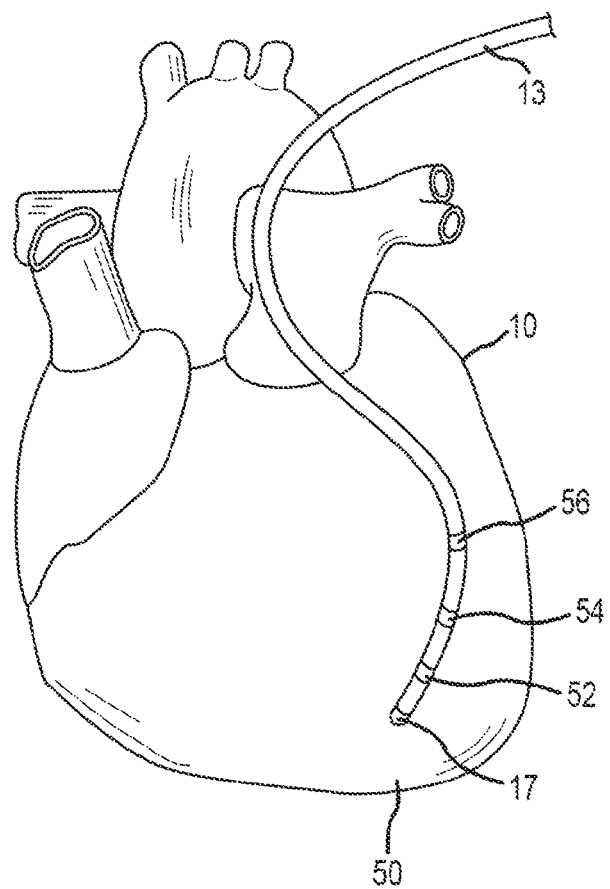
FIG. 2 is a schematic representation of a heart investigated by an electrophysiology catheter with several distal electrodes.
Figure 3:
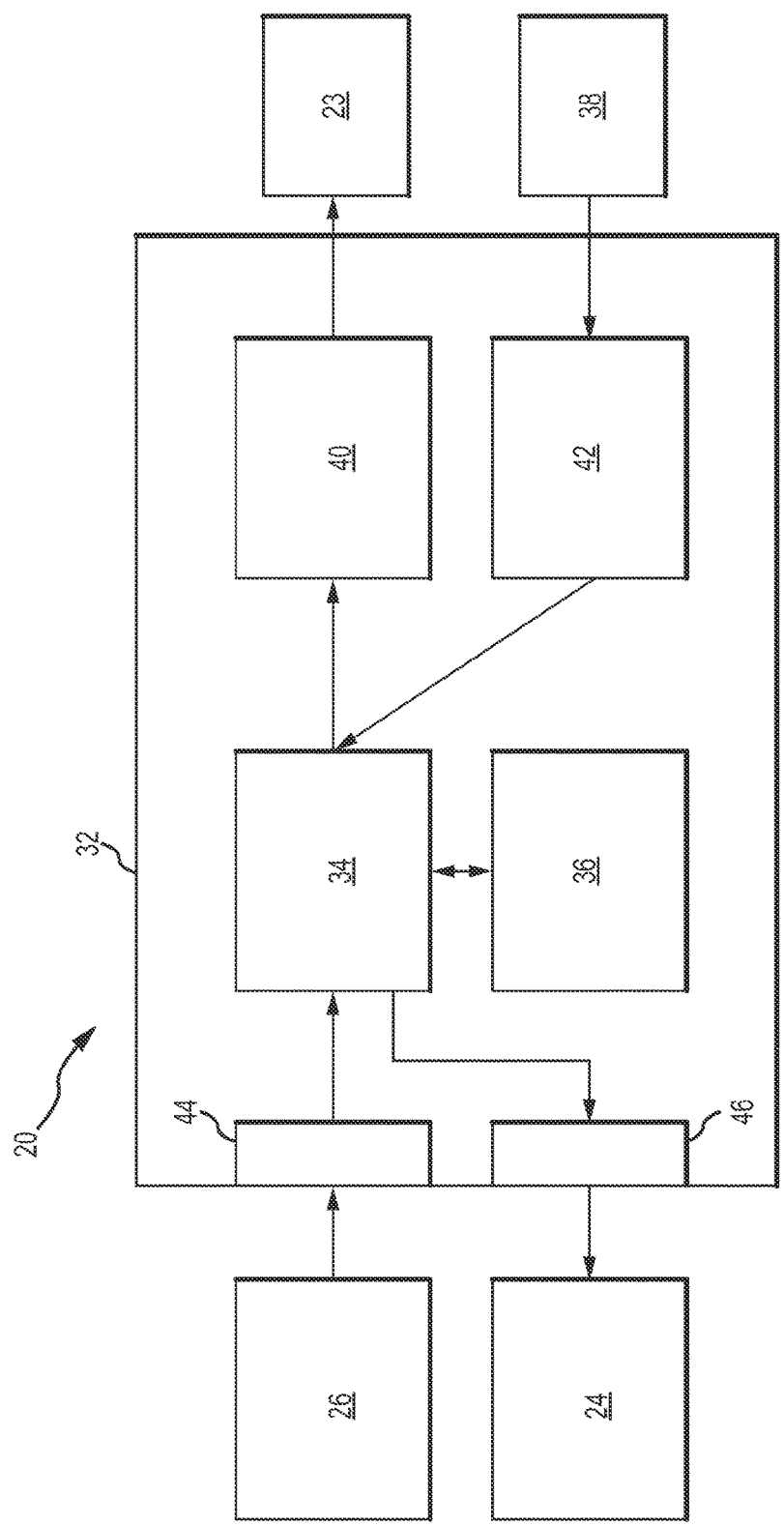
FIG. 3 is a schematic block diagram of a computing device for use in the system shown in FIG. 1.

With reference now to the drawings and in particular to FIGS. 1-3, one example of a suitable mapping system 8 is illustrated for conducting cardiac electrophysiology studies by navigating a cardiac catheter into a heart 10 of a patient 11 to measure electrical activity occurring in the heart and to three-dimensionally map the electrical activity and/or information related to or representative of the electrical activity. The system 8 is particularly used to measure electrophysiology data at a plurality of points along an endocardial surface, and store the measured data in association with location information for each measurement point at which the electrophysiology data was measured.

The patient 11 is depicted schematically in FIG. 1 as an oval for simplicity. Three sets of surface electrodes (e.g., patch electrodes) are shown applied to a surface of the patient 11 along an X-axis, a Y-axis, and a Z-axis. The X-axis surface electrodes 12, 14 are applied to the patient along a first axis, such as on the lateral sides of the thorax region of the patient (e.g., applied to the patient's skin underneath each arm) and may be referred to as the Left and Right electrodes. The Y-axis electrodes 18, 19 are applied to the patient along a second axis generally orthogonal to the X-axis, such as along the inner thigh and neck regions of the patient, and may be referred to as the Left Leg and Neck electrodes. The Z-axis electrodes 16, 22 are applied along a third axis generally orthogonal to the X-axis and the Y-axis, such as along the sternum and spine of the patient in the thorax region and may be referred to as the Chest and Back electrodes. The heart 10 lies between these respective pairs of surface electrodes. An additional surface reference electrode (e.g., a "belly patch") 21 provides a reference and/or ground electrode for the system 8. The belly patch electrode 21 is an alternative to a fixed intra-cardiac electrode 31.

In one suitable embodiment, the localization/mapping system 8 may be the EnSite™ NavX™ navigation and visualization system available from St. Jude Medical, Inc. In other embodiments, any other suitable localization/mapping system may be used.

A representative catheter 13 has an electrode 17 (e.g., a distal electrode), sometimes referred to as the "roving electrode" or "measurement electrode" throughout the specification. Typically, multiple measurement electrodes on catheter 13, or on multiple such catheters, will be used. In one embodiment the system 8 includes up to sixty-four electrodes on up to twelve catheters disposed within the heart and/or vasculature of the patient. In other embodiments, any other suitable number of electrodes and catheters may be used.

An optional fixed reference electrode 31 (e.g., attached to a wall of the heart 10) is also shown on a second catheter 29.

For calibration purposes, this electrode 31 may be stationary (e.g., attached to or near the wall of the heart) or disposed in a fixed spatial relationship with the roving electrode 17. The fixed reference electrode 31 may be used in addition or alternatively to the surface reference electrode 21 described above. In many instances, a coronary sinus electrode or other fixed electrode in the heart 10 is used as a reference for measuring voltages and displacements.

Each surface electrode is coupled to a multiplex switch 24 and the pairs of electrodes are selected by software running on a computer system 20, which couples the electrodes to a signal generator 25. The computer system 20 includes a computing device 32, a display device 23, and an input device 38. The computer system 20 may comprise, for example, a conventional general-purpose computer, a special-purpose computer, a distributed computer, or any other type of computer.

Generally, three nominally orthogonal electric fields are generated by a series of driven and sensed electric dipoles in order to realize catheter navigation in a biological conductor. Alternately, these orthogonal fields can be decomposed and any pairs of surface electrodes can be driven as dipoles to provide effective electrode triangulation. Additionally, such nonorthogonal methodologies add to the flexibility of the system. For any desired axis, the potentials measured across an intra-cardiac electrode 17 resulting from a predetermined set of drive (source-sink) configurations are combined algebraically to yield the same effective potential as would be obtained by simply driving a uniform current along the orthogonal axes. Thus, any two of the surface electrodes 12, 14, 16, 18, 19, 22 may be selected as a dipole source and drain with respect to a ground reference, e.g., the belly patch 21, while the unexcited electrodes measure voltage with respect to the ground reference. The electrode 17 placed in the heart 10 is exposed to the field from a current pulse and is measured with respect to ground, e.g., the belly patch 21. In practice the catheter(s) within the heart may contain multiple electrodes and each electrode potential may be measured. As previously noted, at least one electrode may be fixed to the interior surface of the heart to form a fixed reference electrode 31, which is also measured with respect to ground.

Data sets from each of the surface electrodes, the internal electrodes, and the virtual electrodes may all be used to determine what is referred to herein as a spatial position of the electrode 17 or multiple electrodes positioned within the heart 10. The spatial position of the electrode 17 or electrodes, as referenced herein, means the position of the electrode relative to the patient and/or otherwise independent of the three-dimensional model of the heart.

One of skill in the art will readily appreciate that the measurement electrode 17 can also be used to measure electrophysiology data and system 8 can be used to store the electrophysiology data (e.g., voltage readings, including without limitation, voltage variations over a period of time) in association with location information for the measurement point at which the electrophysiology data was measured. For example, all of the raw electrode voltage data is measured by an A/D converter 26 and stored by the computer system 20 under the direction of software stored in a memory device (not shown in FIG. 1). This electrode excitation process occurs rapidly and sequentially as alternate sets of surface electrodes are selected and the remaining non-driven electrodes are used to measure voltages. This collection of voltage measurements is referred to herein as an "electrode data set." The software has access to each individual voltage measurement made at each electrode during each excitation of each pair of surface electrodes.

The raw electrode data is used by the computer system 20 to determine the spatial position in three-dimensional space (X, Y, Z) of the electrode(s) inside the heart, such as the roving electrode 17, and any number of other electrodes located in or otherwise in proximity to the heart and/or vasculature of the patient 11. FIG. 2 illustrates one catheter 13, which may be a conventional electrophysiology catheter (sometimes referred to as an "EP catheter"), extending into the heart 10. In FIG. 2, the catheter 13 extends into the left ventricle 50 of the heart 10. The catheter 13 includes the distal electrode 17 discussed above with respect to FIG. 1 and has additional electrodes 52, 54, and 56. Because each of these electrodes lies within the patient (e.g., in the left ventricle of the heart), location data may be collected simultaneously for each of the electrodes. In addition, when the electrodes are disposed adjacent to the endocardial surface, although not necessarily directly against the endocardial surface, at least one of the electrodes 17, 52, 54, and 56 can be used to measure electrical activity (e.g., voltage) on the surface of the heart 10.

The data used to determine the spatial location of the electrode(s) 17 within the heart 10 is measured while the surface electrode pairs impress an electric field on the heart. Spatial positions of multiple electrodes 17 may be determined by either sampling electrodes (e.g., sixty-four electrodes spread among up to twelve catheters) simultaneously or in sequence (e.g., multiplexed) and/or by sampling one or more electrodes being moved within the patient (e.g., within a chamber of the heart). In one embodiment, the data is obtained for individual electrodes sampled simultaneously, which allows for collection of data at a single stage or phase of a heartbeat. In another embodiment, position data may be collected either synchronously with one or more phases of the heartbeat or without regard for any particular stage of the heartbeat. Where the data is collected across the phases of the heartbeat, data corresponding to electrode locations along the endocardial surface of the heart will vary with time.

FIG. 3 is a block diagram of the computer system 20. The computer system 20 includes the computing device 32, the display device 23, and the input device 38. The computing device 32 includes a display adapter 40 communicatively coupling the computing device 32 to the display device 23. Display device 23 may include, without limitation, a monitor, a television display, a plasma display, a liquid crystal display (LCD), a display based on light emitting diodes (LED), a display based on a plurality of organic light-emitting diodes (OLEDs), a display based on polymer light-emitting diodes (PLEDs), a display based on a plurality of surface-conduction electron-emitters (SEDs), a display including a projected and/or reflected image or any other suitable electronic device or display mechanism. In one embodiment, display device 23 includes a touch-screen with an associated touch-screen controller. An interface adapter 42 couples the computing device 32 to the input device 38. Computing device 32 includes an input 44 configured to receive electrode signals through A/D converter 26. An output 46 couples control signals from computing device 32 to multiplex switch 24. Input device 38 includes, without limitation, a keyboard, a keypad, a touch-sensitive screen, a mouse, a scroll wheel, a pointing device, an audio input device employing speech-recognition software, and/or any suitable device that enables a user to input data into computing device 32. In some embodiments, input device 38 and display device 23 are integrated into a single input/display device, such as in a touch screen display device.

The computing device 32 includes a processor 34 and a memory device 36 coupled to the processor 34. The term "processor" refers herein generally to any programmable system including systems and microcontrollers, reduced instruction set circuits (RISC), application specific integrated circuits (ASIC), programmable logic circuits, field programmable gate array (FPGA), gate array logic (GAL), programmable array logic (PAL), digital signal processor (DSP), and any other circuit or processor capable of executing the functions described herein. The above examples are exemplary only, and thus are not intended to limit in any way the definition and/or meaning of the term "processor." Moreover, although a single processor is illustrated in FIG. 3, the processor 34 may include more than one processor and the actions described herein may be shared by more than one processor.

The memory device 36 stores program code and instructions, executable by the processor 34. When executed by the processor 34, the program code and instructions cause the processor 34 to operate as described herein. The memory device 36 may include, but is not limited to only include, non-volatile RAM (NVRAM), magnetic RAM (MRAM), ferroelectric RAM (FeRAM), read only memory (ROM), flash memory and/or Electrically Erasable Programmable Read Only Memory (EEPROM). Any other suitable magnetic, optical and/or semiconductor memory, by itself or in combination with other forms of memory, may be included in the memory device 36. The memory device 36 may also be, or include, a detachable or removable memory, including, but not limited to, a suitable cartridge, disk, CD ROM, DVD or USB memory. Although illustrated separate from the processor 34, memory device 36 may be integrated with the processor 34.

Figure 10:
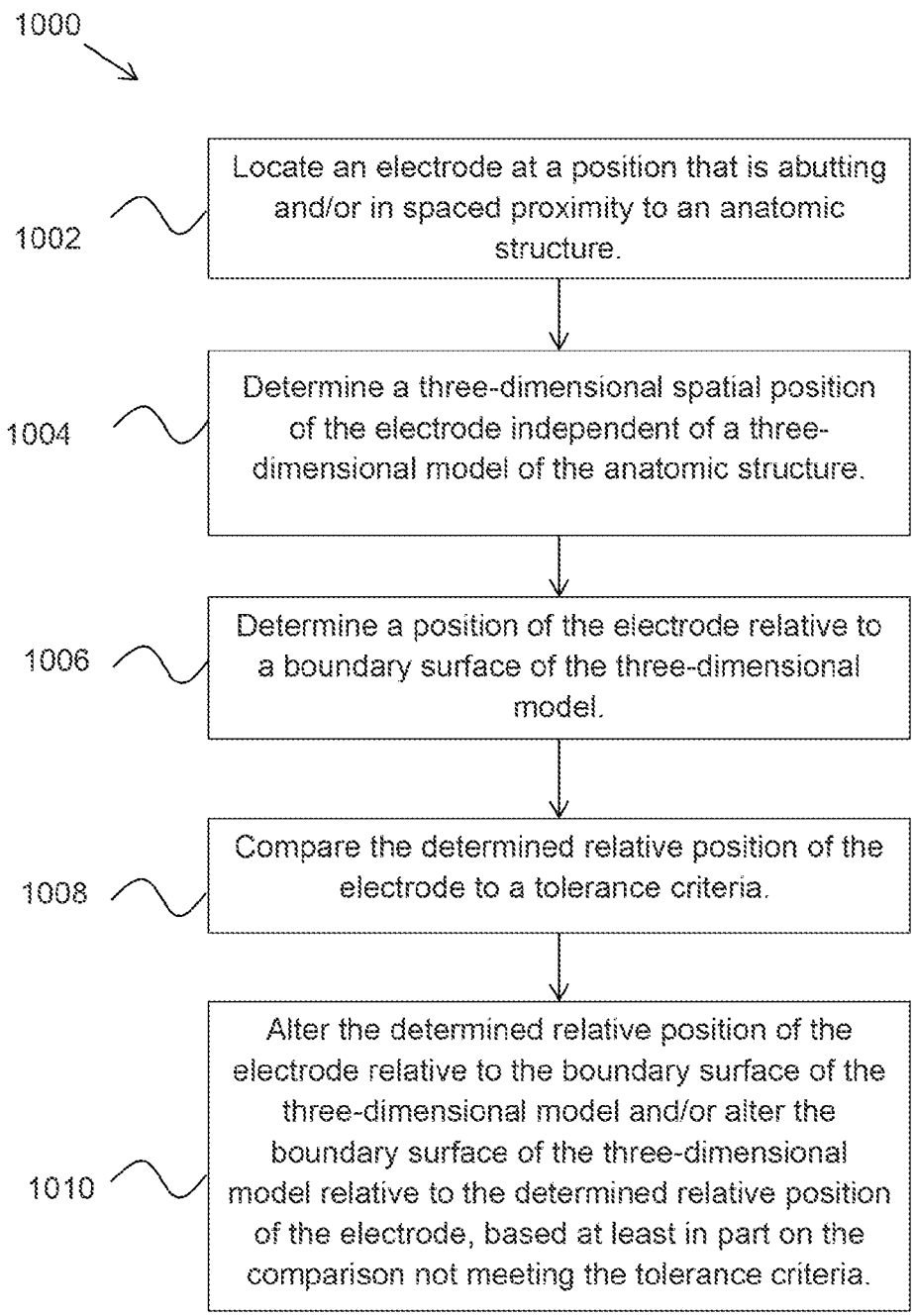
FIG. 10 is a schematic diagram of one embodiment of a method for mapping an anatomic structure.

The memory device 36 stores instructions (e.g., software code) that, when executed by the processor 34, cause the processor 34 to operate as described above and in accordance with the methods set forth herein for correlating the actual position of the one or more electrodes 17 within the patient's heart to the previously generated three-dimensional model of the heart. More particularly, with reference to the schematic diagram 1000 of FIG. 10, one or more electrodes are located 1002 at a position that is abutting and/or in spaced proximity to the anatomic structure (e.g., within the interior of the structure). The instructions executed by the processor 34 cause the computing device 32 to determine 1004 a three-dimensional spatial position of the electrode independent of the three-dimensional model of the anatomic structure. Based on the determined spatial position of the electrode, a position of the electrode relative to the boundary surface of the three-dimensional model is determined 1006. Except as otherwise expressly stated, the position of an electrode relative to a boundary surface of a three-dimensional model is also referred to herein as a "relative electrode position", an "electrode relative position", and/or a "relative position". The instructions further cause the computing device to compare 1008 the determined relative electrode position to a tolerance criterion. In some embodiments, the tolerance criterion is, for example, indicative of whether the relative electrode position lies exterior to the three-dimensional model or lies on or within the interior of the three-dimensional model but otherwise too close to the boundary surface of the three-dimensional model. In response to the tolerance criterion not being satisfied, the determined relative electrode position is altered 1010 and/or the boundary surface of the three-dimensional model relative to the determined relative electrode position. The alteration(s) ensure that the relative electrode position does not lie exterior to the three-dimensional model, and in a particularly suitable embodiment the relative electrode position lies interior to the three-dimensional model in spaced relationship with the boundary surface of the model.

Figure 4A:
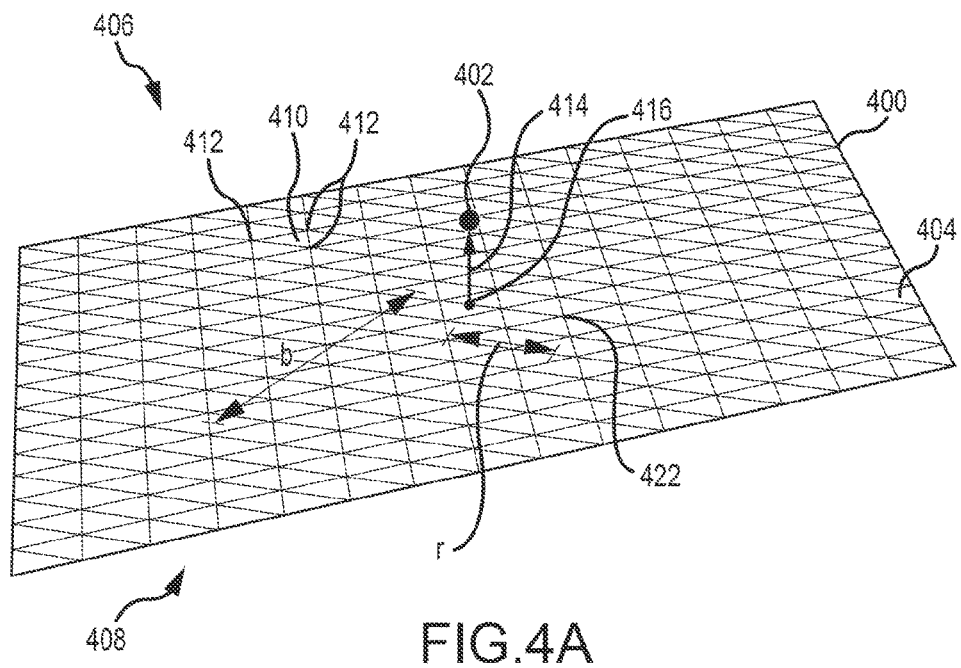
FIG. 4A is a portion of a boundary surface of a three-dimensional model with a position of an electrode shown relative to the boundary surface of the model.
Figure 4B:
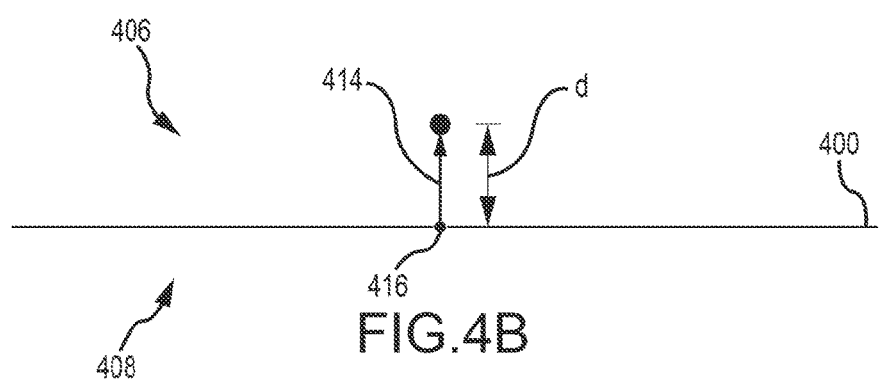
FIG. 4B is a side elevation view of the boundary surface and electrode relative position of FIG. 4A.

FIGS. 4A, 4B, 5A and 5B collectively illustrate one exemplary embodiment in which the computing device 32 alters the distance between the relative electrode position and the boundary surface of the three-dimensional model. For ease of illustration, only a portion of a boundary surface 404 of a three-dimensional model 400 is shown, and in particular is shown in FIGS. 4A and 4B as being a planar portion of the boundary surface. It is understood that the entire three-dimensional model 400 may have any configuration or shape, such as convex, concave, complex curvature, etc., and may be closed such that the three-dimensional model has an interior and an exterior. It is also understood that the portion of the boundary surface 404 of FIG. 4A may be other than planar. In the illustrated embodiment of FIGS. 4A and 4B, an area 408 below the boundary surface 404 is referenced as the first side, or interior of the three-dimensional model 400 and an area 406 above the boundary surface is referenced as the second side, or exterior of the three-dimensional model. The three-dimensional model 400 of FIGS. 4A, 4B, 5A and 5B is a structured mesh of polygons 410 defined by a plurality of vertices 412 and indicative of a linear BEM used to generate the three-dimensional model. Other embodiments may include an unstructured mesh of polygons 410. In the illustrated embodiment, the polygons 410 are triangles—each defined by a set of three vertices 412. It is understood, though, that in other embodiments the polygons may be squares, rectangles, pentagons, hexagons, or any other suitable polygon defined by any suitable number of vertices, or combinations thereof.

FIGS. 4A and 4B also illustrate an initially determined relative position of an electrode 402—determined by the computing device 32 based on the previously determined spatial position of the electrode—i.e., relative to the boundary surface 404 of the three-dimensional model 400. In this embodiment, the relative position of the electrode 402 is thus exterior 406 to the three-dimensional model 400. The computing device 32 determines a distance d from the relative position of the electrode 402 to a closest point 416 on the boundary surface 404 of the three-dimensional model 400, as well as a vector 414 (i.e., a linear path) from the closest point 416 to the relative position of the electrode 402. The distance d is referred to herein as signed distance d, with a positive distance indicating a relative position of the electrode 402 lying exterior 406 to the three-dimensional model and a negative distance indicating a relative position of the electrode lying interior 408 to the three-dimensional model. A relative position of an electrode 402 lying on the boundary surface 404 would have a signed distance d of zero.

The computing device 32, based at least in part on the signed distance d of the position of the electrode 402 relative to the boundary surface 404 of the three-dimensional model 400, compares the signed distance d to a tolerance criterion for the relative position of the electrode 402. For example, in one embodiment the tolerance criterion may require that the signed distance d not be positive (i.e., the relative position of the electrode 402 not lie exterior 406 to the three-dimensional model). In other embodiments, the tolerance criteria may further require that the signed distance d not have a negative value with an absolute value that is less than a threshold value (i.e., the relative position of the electrode is not only interior 408 to the model 400, but is spaced inward from the boundary surface 404 by a threshold value). It will thus be seen in FIGS. 4A and 4B that the relative electrode position 402 illustrated therein is exterior 406 to the model 400 and thus does not satisfy the tolerance criterion.

In response to the tolerance criterion not being satisfied, the computing device 32 alters the signed distance d between the relative position of the electrode 402 and the boundary surface 404 of the three-dimensional model 400. For example, in the exemplary embodiment of FIGS. 5A and 5B, the computing device alters the boundary surface 404 of the three-dimensional model 400 by translating (e.g., expanding) a portion of the boundary surface outward along the vector 414 (e.g., toward the relative position of the electrode 402) until the tolerance criterion is satisfied. For example, in FIGS. 5A and 5B, the tolerance criterion is satisfied once the relative position of the electrode 402 is interior 408 to the three-dimensional model and spaced a threshold value t (FIG. 5B) interior to the boundary surface 404 of the model. That is, the boundary surface 404 of the model 400 at the closest point 416 is moved a distance equal to at least d (the signed distance) and more suitably a distance t+d (i.e., the sum of the threshold value and the signed distance d). In a more particular example, the relative position of the electrode 402 is spaced a threshold distance of at least about 1.5 mm interior to the closest point 416 on the boundary surface 404 of the model 400. It is understood, however, that this threshold distance may be greater than or less than 1.5 mm and remain within the scope of this disclosure.

In a more particular example, to translate the boundary surface 404 of the model 400, each vertex 412 that is within a maximum boundary distance b (along the boundary surface—see FIGS. 4A and 4B) away from the point 416 closest to the relative position of the electrode 402 is translated outward by a computed amount along a vector that is normal to the boundary surface at the vertex 412. The maximum boundary distance b away from the closest point 416 within which the vertices 412 are moved is, in one embodiment, determined at least in part as a function of the signed distance d between the relative position of the electrode 402 and the closest point 416 on the boundary surface 404. The determined amount by which each vertex 412 is translated outward is calculated by the computing device 32 at least in part as a function of the signed distance d, and in other embodiments is further calculated at least in part as a function of a distance r (FIG. 4A) of the vertex to the closest point 416—wherein the distance r may range from zero (where the closest point 416 is at a vertex) to the maximum boundary distance b away from the closest point. Although the distance r is illustrated in FIG. 4A with respect to one particular vertex 422, the distance r is determined for each vertex 412. In one embodiment, the distance r from a vertex 412 to the closest point 416 may be determined by the computing device 32 in Cartesian space, e.g., along a direct line therebetween. In other embodiments, the distance r from a vertex 412 to the closest point 416 may be determined by the computing device 32 by determining the surface distance along the boundary surface (e.g., if the boundary surface is not planar), including but not limited to using geodesics.

The determined amount by which each vertex 412 is translated outward suitably decreases as the distance r of the vertex 412 away from the closest point 416 increases, so as to produce a smooth transition from the unmodified portion (corresponding to the vertices that lie on the boundary surface 404 a distance greater than the maximum boundary distance b away from the closest point 416) of the boundary surface 404 across the modified portion of the boundary surface. In the exemplary embodiment, the maximum boundary distance b from the closest point 416 within which vertices 412 are translated outward is determined by the computing device 32 as a function of the signed distance d. More specifically, in a particularly suitable embodiment all vertices 412 that are within a maximum boundary distance b of five times the distance d (5*d) are translated outward in a direction normal to the boundary surface. Thus, in the embodiment of FIGS. 4A and 4B, all vertices 412 that are within a maximum boundary distance b of five times the signed distance d are moved along a vector normal to each respective vertex 412. Alternatively, the maximum boundary distance b may be a predetermined fixed boundary distance that is independent of the signed distance d of the relative position of the electrode 402. In one example, the maximum boundary distance b may be fixed at fifteen millimeters. It is understood, however, that the maximum boundary distance b may be greater than or less than fifteen millimeters and remain within the scope of this disclosure. Additionally, or alternatively, the maximum boundary distance b may be the lesser of a distance determined as a function of the signed distance d and a predetermined fixed boundary distance.

In one suitable embodiment, the determined amount by which each vertex 412 is translated out is determined by the computing device 32 as a function of at least one of a) the distance r of the vertex away from the closest point 416 and b) the signed distance d of the relative position of the electrode away from the closest point, and more suitably a function of both. In one example, the determined amount by which each vertex 412 is translated outward is determined by the computing device 32 as a cosine function, and more particularly as a cosine function of both the distance r and the signed distance b away from the closest point 416. More specifically, each vertex 412 is translated outward along its own respective vector normal to the boundary surface by an amount equal to $$d*\left(0.5 + 0.5\cos\frac{\pi r}{b}\right) \quad (1)$$

where d is the signed distance d of the relative position of the electrode 402 to the closest point 416 on the boundary surface 404 of the model 400, r is the distance from the vertex 412 to the closest point 416, and b is the maximum boundary distance. Thus, it will be seen that where the closest point 416 lies on a vertex 412, r is zero and the vertex is translated outward a distance equal to the signed distance d along the vector 414. The distance r is illustrated in FIG. 4A to one particular vertex 422, but it is understood that this distance r would be calculated by the computing device 32 for each vertex 412 within the maximum boundary distance b (i.e., 5*d or a predetermined fixed maximum). In alternative embodiments, any other suitable function may be used that produces a relatively smooth perturbation of the boundary surface 404 of the model 400.

Figure 5A:
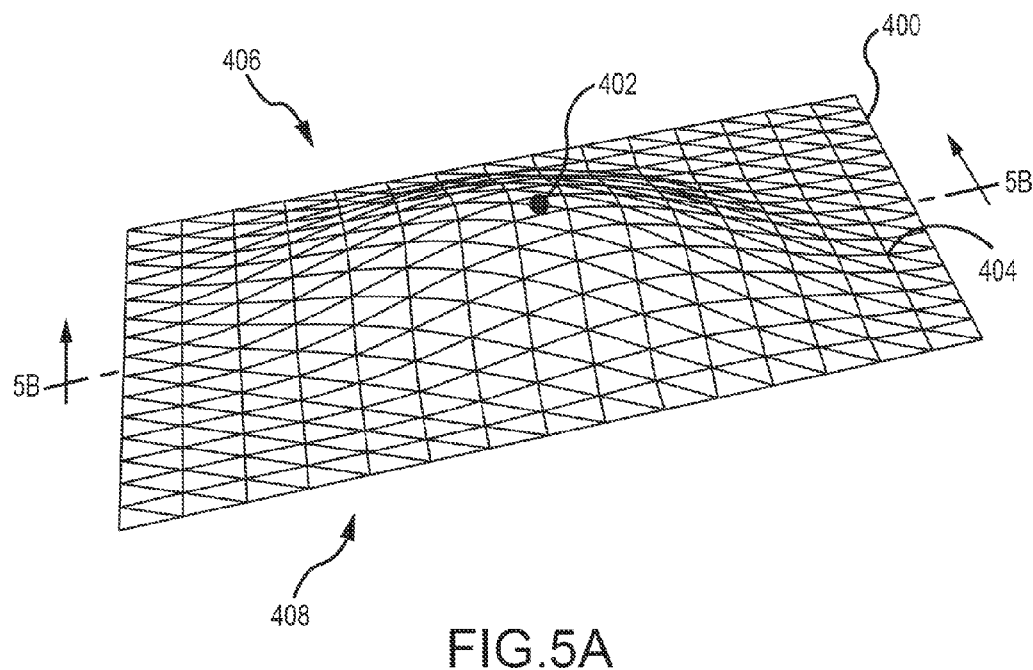
FIG. 5A is the portion of the boundary surface of the three-dimensional model of FIG. 4A with the boundary surface perturbed to alter the relative electrode position.
Figure 5B:
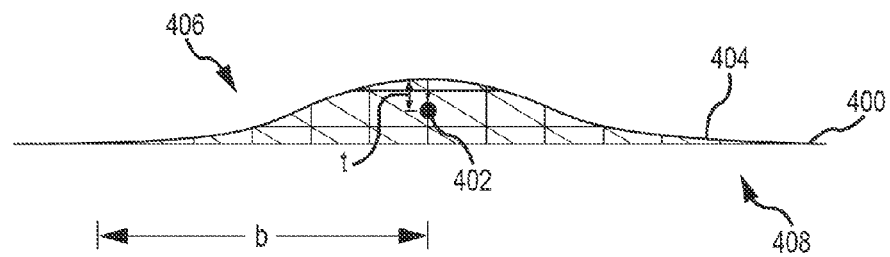
FIG. 5B is a cross-section taken lengthwise through the boundary surface of FIG. 5A.

In the illustrated embodiment of FIGS. 5A and 5B, the distance that the vertices 412 are translated outward further includes an additional predetermined threshold value t (seen best in FIG. 5B). Adding a threshold value t ensures that the electrode position is well within the model 400 (i.e., interior 408 to the model and spaced from the boundary surface 404). The threshold value t may, for example, be directly added to the distance determined using equation (1). The threshold value t in one embodiment is a preset amount that may be varied according to the particular implementation. For example the threshold value t may be smaller in systems used with relatively smaller anatomic structures, systems with greater accuracy of measurement, systems used with more accurate three-dimensional models, etc. In other embodiments, the threshold value t is selectable by a user of the system 8. In still other embodiments, the threshold value t is determined as a function of the signed distance d that the relative position of the electrode 402 is exterior to the three-dimensional model 400. Thus, for example, as the signed distance d increases, the threshold value t may vary.

Although FIGS. 4A, 4B, 5A and 5B are illustrated and described herein with reference to a relative position of the electrode 402 that is exterior 406 to the three-dimensional model 400, the same techniques are equally applicable to electrode positions located interior 408 to the model by a distance that is less than the threshold value t. In such instances, the computing device 32 translates the boundary surface 404 outward away from the relative position of the electrode 402 until the distance of the relative position of the electrode is equal to or greater than the threshold value t.

In the exemplary embodiment of FIGS. 4A, 4B, 5A and 5B, the relative position of a single electrode 402 is illustrated and described. It is understood, however, that multiple measurement electrodes may be used by the mapping system 8, resulting in multiple electrode relative positions being determined by the computing device 32. In one embodiment in which multiple electrode relative positions are determined, the method described above in connection with FIGS. 4A, 4B, 5A and 5B with regard to a single electrode 402 is repeated for each electrode relative position, in no particular order or sequence, until the relative positions of all electrodes are on or interior 408 to the three-dimensional model 400. In other words, it is not necessary that the relative electrode position that is the furthest distance exterior 406 to the model 400 be the first electrode position addressed. In other embodiments, though, the furthest electrode may be treated first within the scope of this disclosure.

Additionally, it is contemplated that while only a portion of the boundary surface 404 of the model 400 was altered (and in the illustrated embodiment of FIGS. 5A and 5B expanded outward), the entire boundary surface may be altered, and more particularly expanded outward, as a function of the signed distance d of the electrode 402 having a relative position that is the furthest away from the boundary surface of the model to assure that the relative positions of all electrodes being monitored lie on or interior to the three-dimensional model. It is also contemplated that while in the exemplary embodiment of FIGS. 5A and 5B the boundary surface 404 of the model 400 is altered to satisfy the tolerance criterion, additionally or alternatively the relative position of the electrode 402 may be altered (e.g., translated inward) such that the relative position of the electrode 402 lies at least on the boundary surface and more suitably lies interior 408 to the three-dimensional model 400.

Figure 6:
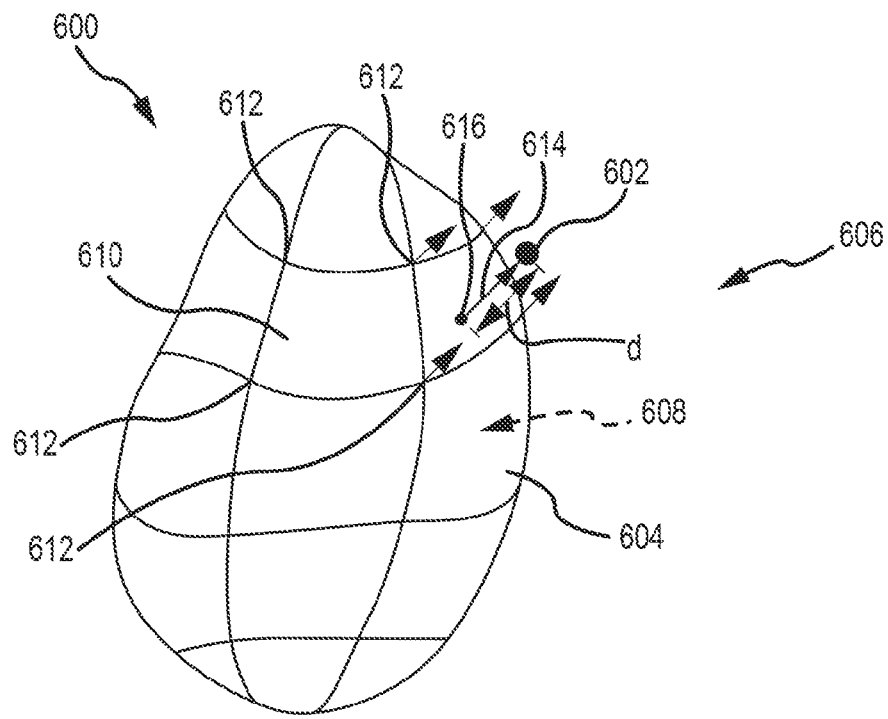
FIG. 6 is a spline boundary element method (BEM) model and an electrode position relative to a boundary surface of the model.
Figure 7:
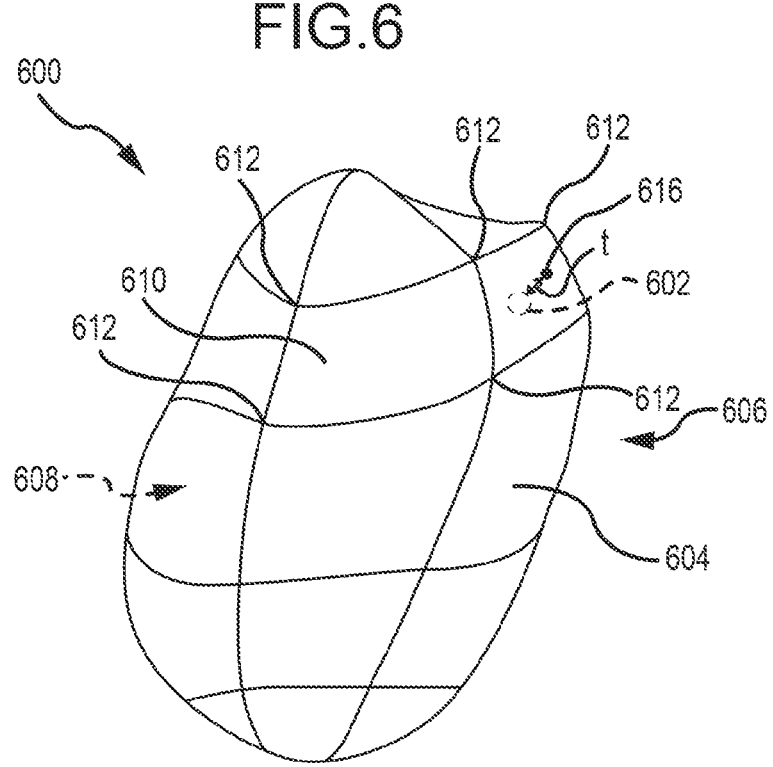
FIG. 7 is the spline BEM model of FIG. 6 perturbed to alter the relative electrode position.

In another embodiment, illustrated in FIGS. 6 and 7, a three-dimensional model 600 of an anatomic structure is shown along with a determined position of an electrode 602 relative to a boundary surface 604 of the model. In this embodiment the three-dimensional model is closed to define an exterior 606 and an interior 608 of the three-dimensional model 600. The three-dimensional model 600 is suitably a tensor-product bicubic spline surface model that represents, for example, a human heart. The boundary surface 604 of the three-dimensional model 600 includes a plurality of grid cells 610, with each grid cell defined by a respective plurality of vertices 612. For example, in the illustrated embodiment the grid cells 610 are generally rectangular (with the exception of those grid cells at the opposite poles) such that the vertices 612 are defined by the four corners of each rectangular grid cell.

FIG. 6 illustrates the initially determined (by the computing device 32) relative position of the electrode 602, i.e., relative to the boundary surface 604 of the three-dimensional model 600. In this embodiment, the relative position of the electrode 602 is exterior 606 to the three-dimensional model 600. The computing device 32 determines a signed distance d from the relative position of the electrode 602 to a closest point 616 on the boundary surface 604 of the three-dimensional model 600, as well as a vector 614 (i.e., a linear path) from the closest point on the boundary surface to the relative position of the electrode. The signed distance d is similar to that described in connection with the previous embodiment, with a positive distance indicating a relative position of the electrode 602 lying exterior 606 to the three-dimensional model 600, a negative distance indicating a relative position of the electrode lying interior 608 to the three-dimensional model, and a distance of zero indicating the relative position of the electrode 602 lying on the boundary surface 604.

The computing device 32, based at least in part on the signed distance d of the relative position of the electrode 602, compares the signed distance d to a tolerance criterion for the relative position of the electrode. For example, in one embodiment the tolerance criterion may require that the signed distance d not be positive (i.e., the relative position of the electrode 602 not lie exterior 606 to the three-dimensional model 600). In other embodiments, the tolerance criterion may further require that the signed distance d not have a negative value, and with the absolute value of the signed distance less than a threshold value t (i.e., the relative position of the electrode is not only interior 608 to the model 600, but is spaced inward from the boundary surface 604 by a threshold value t). It will thus be seen in FIG. 6 that the relative electrode position 602 illustrated therein is exterior 606 to the model 600 and thus does not satisfy the tolerance criterion.

In response to the tolerance criterion not being satisfied, the computing device 32 alters the signed distance d between the relative position of the electrode 602 and the boundary surface 604 of the three-dimensional model 600. For example, in the exemplary embodiment of FIG. 7, the computing device 32 alters the boundary surface 604 of the three-dimensional model 600 by translating (e.g., expanding outward) a portion of the boundary surface parallel to the vector 614 until the tolerance criterion is satisfied. The tolerance criterion may in a particular embodiment be satisfied once the relative position of the electrode 602 is interior 608 to the three-dimensional model 600 and spaced a distance inward away from the boundary surface 604 of the model. In a more particular example, the relative position of the electrode 602 is spaced a distance inward from the boundary surface 604 equal to a threshold value t of at least about 1.5 mm. It is understood, however, that this threshold value t may be greater than or less than 1.5 mm and remain within the scope of this disclosure.

More particularly, in this embodiment the computing device 32 translates the entire grid cell 610 within which the closest point 616 on the boundary surface 604 lies by an amount sufficient to position the electrode 602 in the interior 608 of the model 600, resulting in the altered three-dimensional model 600 shown in FIG. 7. More specifically, each vertex 612 (e.g., corner) of the grid cell 610 within which the closest point 616 lies is moved in a direction parallel to the vector 614 by an amount at least equal to and more suitably greater than the signed distance d. In another embodiment, each vertex 612 of the grid cell 610 within which the closest point 616 lies is moved in the direction of a local surface normal at that vertex 612. In other embodiments, there may be multiple electrodes with respective relative positions and closest points 616 lying within a particular grid cell 610 and not satisfying the tolerance criterion. In such embodiments, the method described above in connection with FIGS. 6 and 7 with regard to a single electrode 602 in the grid cell 610 is repeated for each electrode relative position in the grid cell, in no particular order or sequence, until the relative positions of all electrodes are on or interior to the three-dimensional model 600. In other words, it is not necessary that the relative electrode position that is the furthest distance exterior to the model 600 be the first electrode position addressed. In other embodiments, though, the furthest electrode may be determined first, and the grid cell 610 moved outward as a function of the signed distance of the furthest electrode, and remain within the scope of this disclosure.

In some embodiments, the distance that the vertices 612 are translated outward includes an additional threshold value t. Adding a threshold value t ensures that the electrode position is within the model 600 (i.e., in the interior 608 of model) and spaced inward away from the boundary surface 604. Moreover, although FIGS. 6 and 7 are described with reference to an electrode 602 position that is exterior to the model 600, the same techniques are equally applicable to electrode positions located on the interior 608 of the model 600 by less than the threshold value t. In such instances, the computing device 32 moves the grid cell 610 (in which the closest point 616 lies) outward from the relative position of the electrode 602 until the distance between the relative position of the electrode and the closest point on the boundary surface is equal to or greater than the threshold value t.

Figure 8:
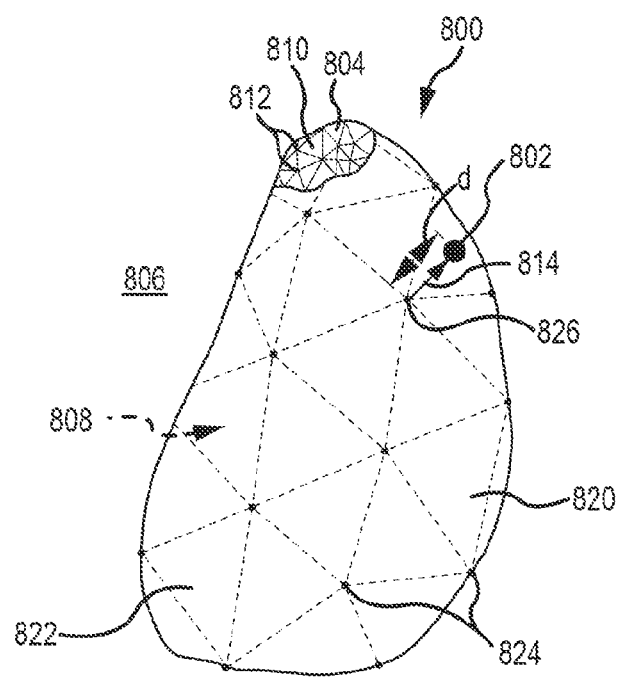
FIG. 8 is a linear BEM model with a control mesh overlay and an electrode position relative to the control mesh.
Figure 9:
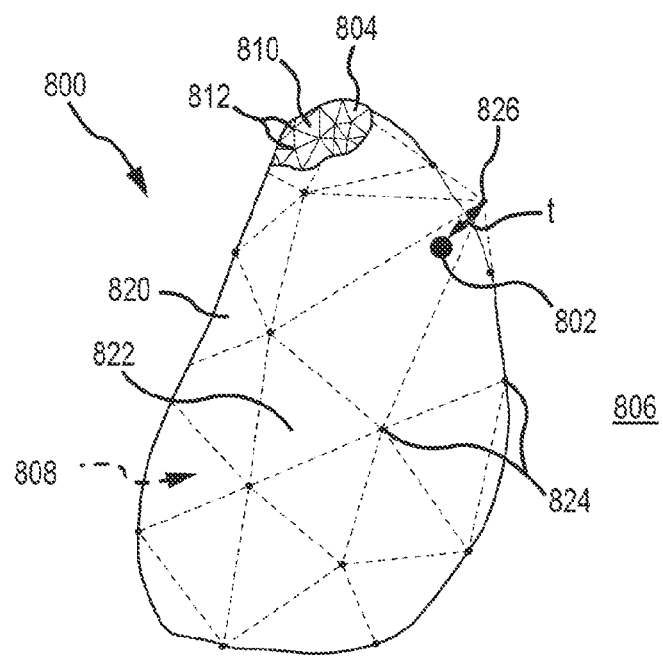
FIG. 9 is the linear BEM model of FIG. 8 perturbed to alter the relative electrode position.

FIGS. 8 and 9 illustrate another embodiment in which a three-dimensional model 800 of an anatomic structure is shown along with a determined position of an electrode 802 relative to a boundary surface 804 of the model. In this embodiment the three-dimensional model 800 is closed to define an exterior 806 and an interior 808 of the three-dimensional model 800. The three-dimensional model 800 is a standard linear triangulated surface model (e.g., similar to the boundary surface 404 of the embodiment of FIGS. 4A and 4B) defined by triangular cells 810 having respective vertices 812, but is modified by the computing device 32 using a mean value coordinates method in which a control mesh 820 surrounds (e.g., overlays) the boundary surface 804 of the model 800. One example of a suitable mean value coordinate method is described in "Mean Value Coordinates for Closed Triangular Meshes" by Ju, T., et al. (2005), published in *ACM Transactions on Graphics,* 24(3):561-566. The illustrated control mesh 820 includes triangular cells 822 having nodes 824. In other embodiments, the cells 822 of the control mesh 820 may be any other suitable polygonal shape. As described in further detail below, the boundary surface 804 of the three-dimensional model 800 of this embodiment is altered by manipulating the control mesh 820 and moving the boundary surface according to a function defined by the movement of the control mesh.

FIG. 8 illustrates the initially determined relative position of the electrode 802 (based on the spatial position thereof), i.e., relative to the boundary surface 804 and more particularly the control mesh 820. In this embodiment, the computing device 32 determines a signed distance (not shown) from the relative position of the electrode 802 to a closest point (not shown) on the boundary surface 804 of the three-dimensional model 800. The signed distance is similar to that described in connection with the previous embodiments, with a positive distance indicating a relative position of the electrode 802 lying exterior 806 to the three-dimensional model 800, a negative distance indicating a relative position of the electrode lying interior 808 to the three-dimensional model, and a distance of zero indicating the relative position of the electrode 802 lying on the boundary surface 804.

The computing device 32, based at least in part on the signed distance d of the relative position of the electrode 802, compares the signed distance to a tolerance criterion for the relative position of the electrode. For example, in one embodiment the tolerance criterion may require that the signed distance not be positive (i.e., the relative position of the electrode 802 not lie exterior 806 to the three-dimensional model 800). In other embodiments, the tolerance criterion may further require that the signed distance d not have a negative value with an absolute value of the signed distance less than a threshold value t (i.e., the relative position of the electrode is not only interior 808 to the model 800, but is spaced inward from the boundary surface 804 by a threshold value t). In the embodiment of FIG. 8, the relative position of the electrode 802 is exterior 806 to the model 800 and thus does not satisfy the tolerance criterion.

In response to the relative position of the electrode 802 not satisfying the tolerance criterion, the computing device 32 determines the nearest vertex 812 to the determined closest point on the boundary surface 804 of the model 800. Once the nearest vertex 812 is determined, the control mesh 820 is generated using mean value coordinates, with a main node 826 of the control mesh at the determined nearest vertex 812 as illustrated in FIG. 8. Additional nodes 824 in the control mesh 804 are selected surrounding the main node 826. The additional nodes 824 are selected to correspond to vertices 812 of the boundary surface 804 and at a distance from the main node 826 that is sufficient to permit the boundary surface 804 to deform in the vicinity of the main node 826 of the control mesh. In one embodiment, twenty control nodes 824 are selected around the main node 826 at, or near, the vertices of an icosahedron.

The computing device 32 also determines a distance d from the main node 826 to the relative position of the electrode 802, as well as a vector (e.g., linear path) 814 from the main node 826 to the relative position of the electrode. The main node 826 of the control mesh 820 (and hence the associated underlying boundary surface 804) is altered and more particularly translated outward along the vector 814 at least the distance d from the main node 826 to the relative position of the electrode 802, and in an exemplary embodiment greater than the distance d such that the relative electrode position is located interior 808 to the model 800 following translation of the main node 826 as illustrated in FIG. 9.

In other embodiments, there may be multiple electrodes 802 that have respective relative positions that do not satisfy the tolerance criterion. In such embodiments, the method described above in connection with FIGS. 8 and 9 with regard to a single electrode 802 is repeated for each electrode relative position, in no particular order or sequence, until the relative positions of all electrodes are on or more suitably interior to the three-dimensional model 800. In other words, it is not necessary that the relative electrode position that is the furthest distance exterior to the model 800 be the first electrode position addressed. In other embodiments, though, the furthest electrode may be addressed first, or the electrodes may be ordered with respect to some other criterion, and remain within the scope of this disclosure.

In some embodiments, the distance that the main node 826 is translated outward further includes an additional threshold value t (not shown). Adding a threshold value t ensures that the electrode position is within the model 800 (i.e., in the interior 808 of the model) and spaced inward away from the boundary surface 804. Moreover, although FIGS. 8 and 9 are described with reference to an electrode 802 position that is exterior to the model 800, the same techniques are equally applicable to electrode positions located on the interior 808 of the model 800 by less than the threshold value t. In such instances, the computing device 32 moves the main node 826 outward until the distance between the relative position of the electrode and the main node is equal to or greater than the threshold value t.

The system 8 performs the above-described alterations to the three-dimensional model 400, 600, 800 independently for temporally separated electrode data. For example, when the system 8 captures electrode data over a period of time, a number of temporally separated sets of data are collected. Each set of data may include electrode data from some or all of the electrodes in the heart. The electrode positions for each set of data are calculated relative to the original three-dimensional anatomic structure and the techniques described above are applied for that set of electrode positions relative to the original three dimensional object. No set of electrode data calculates its electrode positions relative to the three dimensional model as modified based on a different set of electrode data.

Although certain embodiments of this disclosure have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

When introducing elements of the present disclosure or the various versions, embodiment(s) or aspects thereof, the articles "a", "an", "the" and "said" are intended to mean that there are one or more of the elements. The terms "comprising", "including" and "having" are intended to be inclusive and mean that there may be additional elements other than the listed elements. The use of terms indicating a particular orientation (e.g., "top", "bottom", "side", etc.) is for convenience of description and does not require any particular orientation of the item described.

As various changes could be made in the above without departing from the scope of the disclosure, it is intended that all matter contained in the above description and shown in the accompanying drawings shall be interpreted as illustrative and not in a limiting sense.

What is claimed is:

1. A computer implemented method for modeling the spatial position of an electrode relative to a three-dimensional model of an anatomic structure, the three-dimensional model having a boundary surface that defines an exterior side of the three-dimensional model and an interior side of the three-dimensional model, the computer implemented method comprising:
    locating the electrode at a position that is at least one of abutting and in spaced proximity to the anatomic structure;
    determining a three-dimensional spatial position of the electrode independent of the three-dimensional model of the anatomic structure;
    determining, based at least in part on the determined three-dimensional spatial location of the electrode, a position of the electrode relative to the boundary surface of the three-dimensional model and a signed distance (d) between said determined relative electrode position and a point on the boundary surface of the three-dimensional model that is closest to the electrode, wherein the signed distance (d) indicates whether said determined relative electrode position is exterior or interior to the three-dimensional model;
    comparing the signed distance (d) to a tolerance criterion, wherein the tolerance criterion requires that the determined relative electrode position is interior to the three-dimensional model and spaced inward from the boundary surface of the three-dimensional model by a predetermined threshold distance value (t); and
    based at least in part on the comparison not meeting the tolerance criterion, altering the boundary surface of the three-dimensional model such that the boundary surface at the closest point to said determined relative electrode position is moved a distance equal to a sum of the predetermined threshold distance value (t) and the signed distance (d), such that the relative position of the electrode is interior to the three-dimensional model and spaced inward from the altered boundary surface of the three-dimensional model by the predetermined threshold distance value (t).

2. The computer implemented method of claim 1 wherein altering the boundary surface comprises translating at least a portion of the boundary surface of the three-dimensional model.

3. The computer implemented method of claim 2 wherein translating at least a portion of the boundary surface of the three-dimensional model comprises translating at least a portion of the boundary surface of the three-dimensional model outward by an amount greater than the signed distance (d).

4. The computer implemented method of claim 2 wherein the three-dimensional model comprises a spline model including a plurality of grid cells with each grid cell including a plurality of vertices, and wherein translating at least a portion of the surface of the three-dimensional model comprises translating, in a direction parallel to a vector from the closest point on the boundary surface to the determined relative electrode position, the plurality of vertices of a grid cell within which the closest point lies.

5. The computer implemented method of claim 2 wherein the three-dimensional model comprises a polygon mesh including a plurality of cells each having a plurality of vertices, and wherein translating at least a portion of the boundary surface of the three-dimensional model comprising translating each vertex that is less than a determined distance (b) along the boundary surface away from the closest point outward by a determined amount, said determined amount being a function of at least one of a) a distance (r) of each respective vertex along the boundary surface to the closest point on the boundary surface and b) the determined distance of the relative electrode position from the closest point on the boundary.

6. A non-contact system for modeling the spatial position of an electrode relative to a three-dimensional model of an anatomic structure, the three-dimensional model having a boundary surface that defines an exterior side of the three-dimensional model and an interior side of the three-dimensional model, the non-contact system comprising:
    a computing device configured to receive signals from electrode, the signals corresponding to a position of the electrode at a position that is at least one of abutting and in spaced proximity to the anatomic structure, the computing device comprising:
    a processor; and
    at least one memory device coupled to said processor, the memory device storing the three-dimensional model of the anatomic structure and computer-executable instructions that, when executed by the processor, cause the computing device to:
        determine a position of the electrode relative to the boundary surface of the three-dimensional model and a signed distance (d) between said determined relative electrode position and a point on the boundary surface of the three-dimensional model that is closest to the electrode,
            wherein the signed distance (d) indicates whether said determined relative electrode position is exterior or interior to the three-dimensional model;
        compare the signed distance (d) to a tolerance criterion,
            wherein the tolerance criterion requires that the determined relative electrode position is interior to the three-dimensional model and spaced inward from the boundary surface of the three-dimensional model by a predetermined threshold distance value (t); and
        based at least in part on the comparison not meeting the tolerance criterion, alter the boundary surface of the three-dimensional model such that the boundary surface at the closest point to said determined relative electrode position is moved a distance equal to a sum of the predetermined threshold distance value (t) and the signed distance (d), such that the relative position of the electrode is interior to the three-dimensional model and spaced inward from the altered boundary surface of the three-dimensional model by the predetermined threshold distance value (t).

7. The non-contact system of claim 6 wherein the memory device stores computer-executable instructions that, when executed by the processor, cause the processor to alter the boundary surface of the three-dimensional model relative to the determined relative electrode position by translating at least a portion of the boundary surface of the three-dimensional model.

8. The non-contact system of claim 7 wherein translating at least a portion of the boundary surface of the three-dimensional model comprises translating at least a portion of the boundary surface of the three-dimensional model outward by an amount greater than the signed distance (d).

9. The non-contact system of claim 7 wherein the three-dimensional model comprises a spline model including a plurality of grid cells with each grid cell including a plurality of vertices, and wherein translating at least a portion of the surface of the three-dimensional model comprises translating, in a direction parallel to a vector from the closest point on the boundary surface to the determined relative electrode position, the plurality of vertices of a grid cell within which the closest point lies.

10. The non-contact system of claim 9 wherein the computing device is configured to receive signals from a plurality of electrodes located at respective positions that are at least one of abutting and in spaced proximity to the anatomic structure, the memory device storing computer-executable instructions that, when executed by the processor, cause the computing device to determine a relative electrode position, compare the determined relative electrode position, and determine a point on the boundary surface for each of the plurality of electrodes, wherein in the event that more than one of said determined points lie within one of said grid cells, the translating is conducted one of a) in a single instance by determining which of the relative electrode positions is furthest away from its respective determined point and translating the plurality of vertices of the grid cell by an amount greater than or equal to the determined distance between said determined point and the determined relative electrode position of the further away electrode and b) for each relative electrode position until the relative electrode positions of all electrodes having a respective determined point within the grid cell have been subjected to the translating.

* * * * *